(12) United States Patent
Fujii et al.

(10) Patent No.: US 11,906,465 B2
(45) Date of Patent: Feb. 20, 2024

(54) MAGNETIC MATERIAL CONCENTRATION MEASURING DEVICE

(71) Applicants: MITSUI E&S DU CO., LTD., Aioi (JP); MEIYO ELECTRIC CO., LTD., Shizuoka (JP)

(72) Inventors: Takashi Fujii, Aioi (JP); Shigeki Kagomiya, Shizuoka (JP)

(73) Assignees: MITSUI E&S DU CO., LTD., Aioi (JP); MEIYO ELECTRIC CO., LTD., Shizuoka (JP)

( * ) Notice: Subject to any disclaimer, the term of this patent is extended or adjusted under 35 U.S.C. 154(b) by 121 days.

(21) Appl. No.: 17/575,807

(22) Filed: Jan. 14, 2022

(65) Prior Publication Data

US 2022/0137001 A1 May 5, 2022

Related U.S. Application Data

(63) Continuation of application No. PCT/JP2019/032289, filed on Aug. 19, 2019.

(51) Int. Cl.
*G01N 27/74* (2006.01)

(52) U.S. Cl.
CPC .................................... *G01N 27/74* (2013.01)

(58) Field of Classification Search
CPC ............... G01N 27/74; G01N 33/5434; G01N 35/0098; G01N 2035/00564;
(Continued)

(56) References Cited

U.S. PATENT DOCUMENTS

| 5,315,243 A * | 5/1994 | Kempster .......... G01N 15/0656 |
| | | 324/204 |
| 8,037,740 B2 * | 10/2011 | Fujii .................... G01N 27/08 |
| | | 324/228 |

(Continued)

FOREIGN PATENT DOCUMENTS

| JP | 2001-153844 A | 6/2001 |
| JP | 2008-008885 A | 1/2008 |

(Continued)

OTHER PUBLICATIONS

Extended European Search Report dated Aug. 11, 2023, in corresponding European Patent Application No. 19941787.4, 8 pages.

(Continued)

*Primary Examiner* — Vinh P Nguyen

(74) *Attorney, Agent, or Firm* — Oblon, McClelland, Maier & Neustadt, L.L.P.

(57) ABSTRACT

Provided is a magnetic material concentration measuring device including: a bobbin having an outer circumference around which an exciting coil, an output coil, and a further exciting coil are wound; an eccentric hole formed in the bobbin; a rotor that is rotatably fitted in the eccentric hole about an eccentric axis line; a first cutout part that forms a first flow passage on one end side in an eccentric axis line direction of the rotor; a second cutout part that forms a second flow passage whose angle is shifted in a rotor rotation direction with respect to the first cutout part, on another end side in the eccentric axis line direction of the rotor; and a communication passage that connects the first flow passage and the second flow passage.

7 Claims, 12 Drawing Sheets

(58) Field of Classification Search
CPC .. G01N 33/2858; G01N 27/023; G01N 27/72; G01N 33/54326; G01N 2015/1087; G01N 27/76; G01N 15/02; G01N 21/6447; G01N 21/8803; G01N 15/04; G01N 2015/0038; G01N 33/2835; G01N 15/0656; G01N 2015/0681; G01N 27/08; G01N 27/00; G01R 33/1215; G01R 33/34; G01R 33/12; G01R 33/385; G01R 31/00; G01R 33/1223; G01R 33/563; A61B 5/0515; H04B 5/0087; C02F 1/488; G01P 3/487; G01P 3/488

See application file for complete search history.

(56) References Cited

U.S. PATENT DOCUMENTS

| | | | |
|---|---|---|---|
| 8,115,478 B2* | 2/2012 | Fujii | G01N 27/74 |
| | | | 324/204 |
| 8,816,674 B2* | 8/2014 | Ukai | G01N 33/2835 |
| | | | 324/204 |
| 2009/0189599 A1 | 7/2009 | Fujii et al. | |

FOREIGN PATENT DOCUMENTS

| | | |
|---|---|---|
| JP | 2011-133292 A | 7/2011 |
| JP | 2013-190293 A | 9/2013 |

OTHER PUBLICATIONS

International Search Report dated Nov. 19, 2019 in PCT/JP2019/032289 filed on Aug. 19, 2019, 1 page.

* cited by examiner

MAGNETIC MATERIAL CONCENTRATION MEASURING DEVICE

TECHNICAL FIELD

The present disclosure relates to a magnetic material concentration measuring device.

BACKGROUND ART

Generally, in a machine such as a large marine diesel engine including a piston or other reciprocating parts, a piston ring and a cylinder liner wear along with sliding motions of the piston ring with respect to the cylinder liner.

If the wearing becomes advanced, a smooth operation of the machine is hindered, and hence it is extremely important to grasp the sliding state of the piston ring with respect to the cylinder liner while the machine is in operation.

As the machine is continuously in operation, wear debris containing a magnetic material such as iron powder mixes into lubricant for the machine. Accordingly, the concentration of the magnetic material contained in the collected lubricant is measured, whereby the sliding state of the piston ring with respect to the cylinder liner is grasped and the supply amount of the lubricant is adjusted and optimized.

For a magnetic material concentration measuring device that has been invented by the present inventors and has already been patented, see, for example, Patent Literature 1.

The magnetic material concentration measuring device includes: exciting coils to which alternating voltage is applied, the exciting coils being provided on an outer circumference of a flow passage through which a fluid containing a magnetic material, such as lubricant, flows; an output coil from which an alternating voltage signal is output, the output coil being provided in proximity to the exciting coils; and a signal processor that obtains a concentration of the magnetic material on a basis of a change in the alternating voltage signal output from the output coil.

Further, in the magnetic material concentration measuring device, a mechanism that converts a rotating motion of a drive device into a reciprocating motion of a piston is used, whereby the fluid is guided into/out of the flow passage.

CITATION LIST

Patent Literature

Patent Literature 1: JP 5165269 B2

SUMMARY

Technical Problem

However, the use of the mechanism that converts the rotating motion into the reciprocating motion of the piston as described above has a problem that there are many restrictions in the installation of the magnetic material concentration measuring device.

Further, if the fluid is guided into/out of the flow passage by the reciprocating motion of the piston, replacement of the fluid is difficult, this may influence the accuracy of a measurement value, and there thus remains room for improvement.

In view of the above-mentioned conventional problems, the present disclosure discloses a magnetic material concentration measuring device capable of increasing the degree of freedom in the installation thereof and achieving enhancement in the accuracy of a measurement value.

Solution to Problem

The present disclosure relates to a magnetic material concentration measuring device including: exciting coils to which alternating voltage is applied, the exciting coils being provided on an outer circumference of a flow passage through which a fluid containing a magnetic material flows; an output coil from which an alternating voltage signal is output, the output coil being provided in proximity to the exciting coils; and a signal processor that obtains a concentration of the magnetic material on a basis of a change in the alternating voltage signal output from the output coil, the magnetic material concentration measuring device including: a bobbin having an outer circumference around which the exciting coil, the output coil, and the exciting coil are wound; an eccentric hole that is eccentrically formed so as to penetrate in an axis line direction of the bobbin; a rotor that is rotatably fitted in the eccentric hole about an eccentric axis line; a first cutout part that forms a first flow passage on one end side in an eccentric axis line direction of the rotor; a second cutout part that forms a second flow passage whose angle is shifted in a rotor rotation direction with respect to the first cutout part, on another end side in the eccentric axis line direction of the rotor; and a communication passage that is formed in the rotor so as to connect the first flow passage and the second flow passage.

The magnetic material concentration measuring device can include a transfer drive mechanism that circulates the fluid through the first flow passage, the communication passage, and the second flow passage while rotating the rotor.

In the magnetic material concentration measuring device, the transfer drive mechanism can include: a drive shaft that is rotationally driven by a drive device and is connected to the rotor so as to extend in the eccentric axis line direction; and a spiral blade provided on an outer circumference of the drive shaft.

Further, in the magnetic material concentration measuring device, the transfer drive mechanism can include: a drive shaft that is rotationally driven by a drive device and is connected to the rotor so as to extend in the eccentric axis line direction; a transfer shaft provided in parallel with the drive shaft; a transmission mechanism that transmits rotation of the drive shaft to the transfer shaft; and a spiral blade provided on an outer circumference of the transfer shaft.

The present disclosure also relates to a magnetic material concentration measuring device including: exciting coils to which alternating voltage is applied, the exciting coils being provided on an outer circumference of a flow passage through which a fluid containing a magnetic material flows; an output coil from which an alternating voltage signal is output, the output coil being provided in proximity to the exciting coils; and a signal processor that obtains a concentration of the magnetic material on a basis of a change in the alternating voltage signal output from the output coil, the magnetic material concentration measuring device including: a bobbin having an outer circumference around which the exciting coil, the output coil, and the exciting coil are wound; an eccentric hole that is eccentrically formed so as to penetrate in an axis line direction of the bobbin; and a uniaxial eccentric screw pump that is fitted in the eccentric hole and circulates the fluid.

In the magnetic material concentration measuring device, the uniaxial eccentric screw pump can include: a stator inside of which a spiral flow passage is formed; and a rotor that is rotatably fitted in the stator and forms a continuous cavity independent of the spiral flow passage, and the exciting coils between which the output coil is located can be respectively wound at outer circumferential positions of the bobbin corresponding to positions with respect to each of which the cavity is formed so as to be shifted by 90 degrees in a rotor rotation direction.

Further, in the magnetic material concentration measuring device, the uniaxial eccentric screw pump may include: a stator inside of which a spiral flow passage is formed; and a rotor that is rotatably fitted in the stator and forms a continuous cavity independent of the spiral flow passage, and the exciting coils between which the output coil is located may be respectively wound such that there is at least a difference in a distance with respect to the cavity, at outer circumferential positions of the bobbin corresponding to positions with respect to each of which the cavity is formed so as to be shifted by 180 degrees in a rotor rotation direction.

Effects

The magnetic material concentration measuring device of the present disclosure can produce excellent effects of increasing the degree of freedom in the installation thereof and achieving enhancement in the accuracy of a measurement value.

DESCRIPTION OF EMBODIMENTS

Hereinafter, embodiments of the present disclosure are described with reference to the attached drawings.

FIG. 1 to FIG. 5 illustrate a first embodiment of a magnetic material concentration measuring device of the present disclosure.

Figure 1:
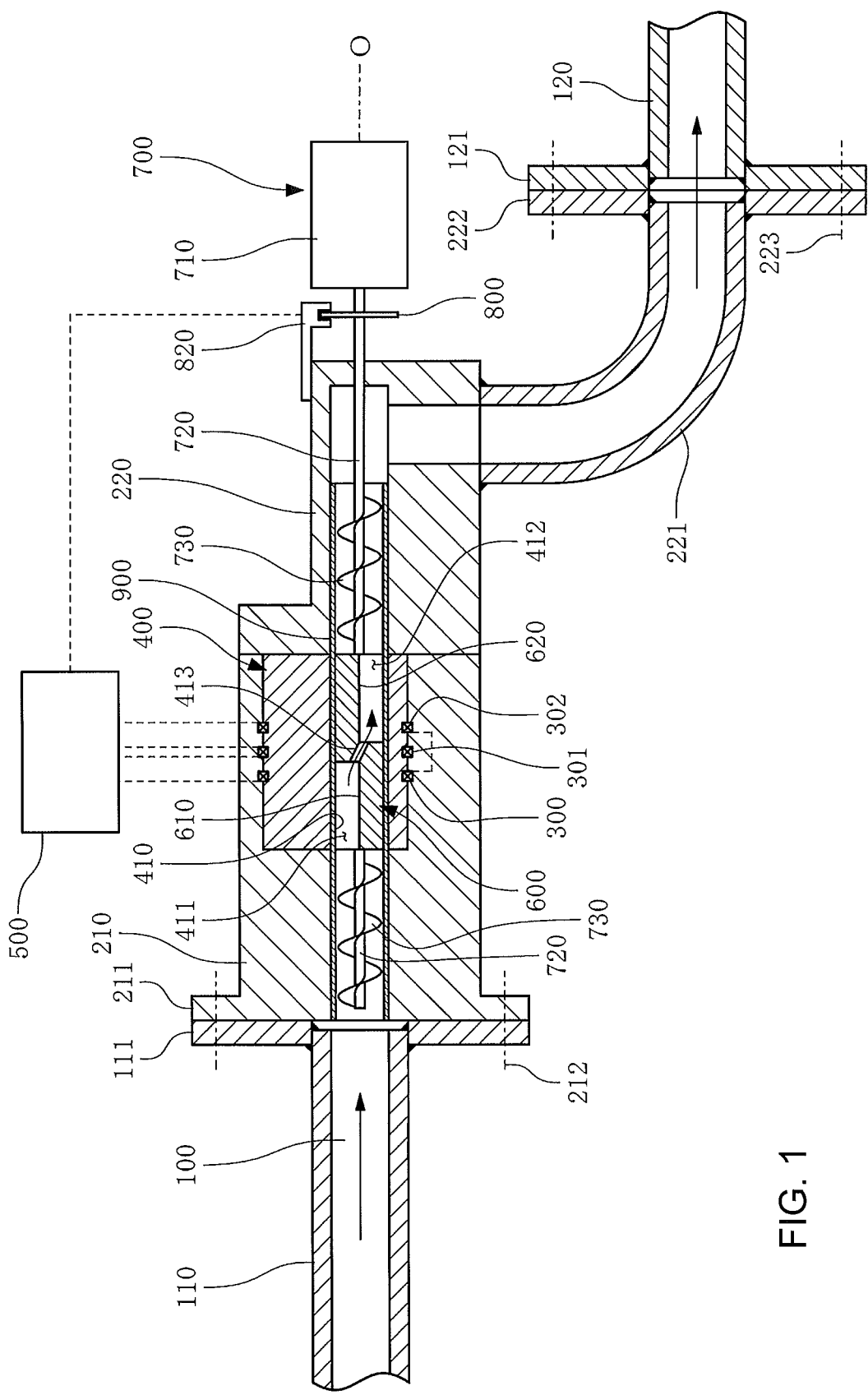
FIG. 1 is a cross-sectional view illustrating a first embodiment of a magnetic material concentration measuring device of the present disclosure.

As illustrated in FIG. 1, a magnetic material concentration measuring device of the first embodiment is configured by providing a measuring device main body 200 between an inflow pipe 110 and an outflow pipe 120 that form a flow passage 100 through which a fluid containing a magnetic material flows.

The measuring device main body 200 includes: an inflow casing 210 whose flange 211 is connected to a flange 111 of the inflow pipe 110 by a fastening member 212; an outflow casing 220 integral with the inflow casing 210; and a nozzle part 221 that is bended to extend from the outflow casing 220. Note that a flange 222 of the nozzle part 221 is connected to a flange 121 of the outflow pipe 120 by a fastening member 223.

A bobbin 400 having an outer circumference around which an exciting coil 300, an output coil 301, and an exciting coil 302 are wound is fitted in the inflow casing 210. The material of the bobbin 400 may be a non-magnetic substance (having a relative magnetic permeability of roughly 1).

Figure 2:
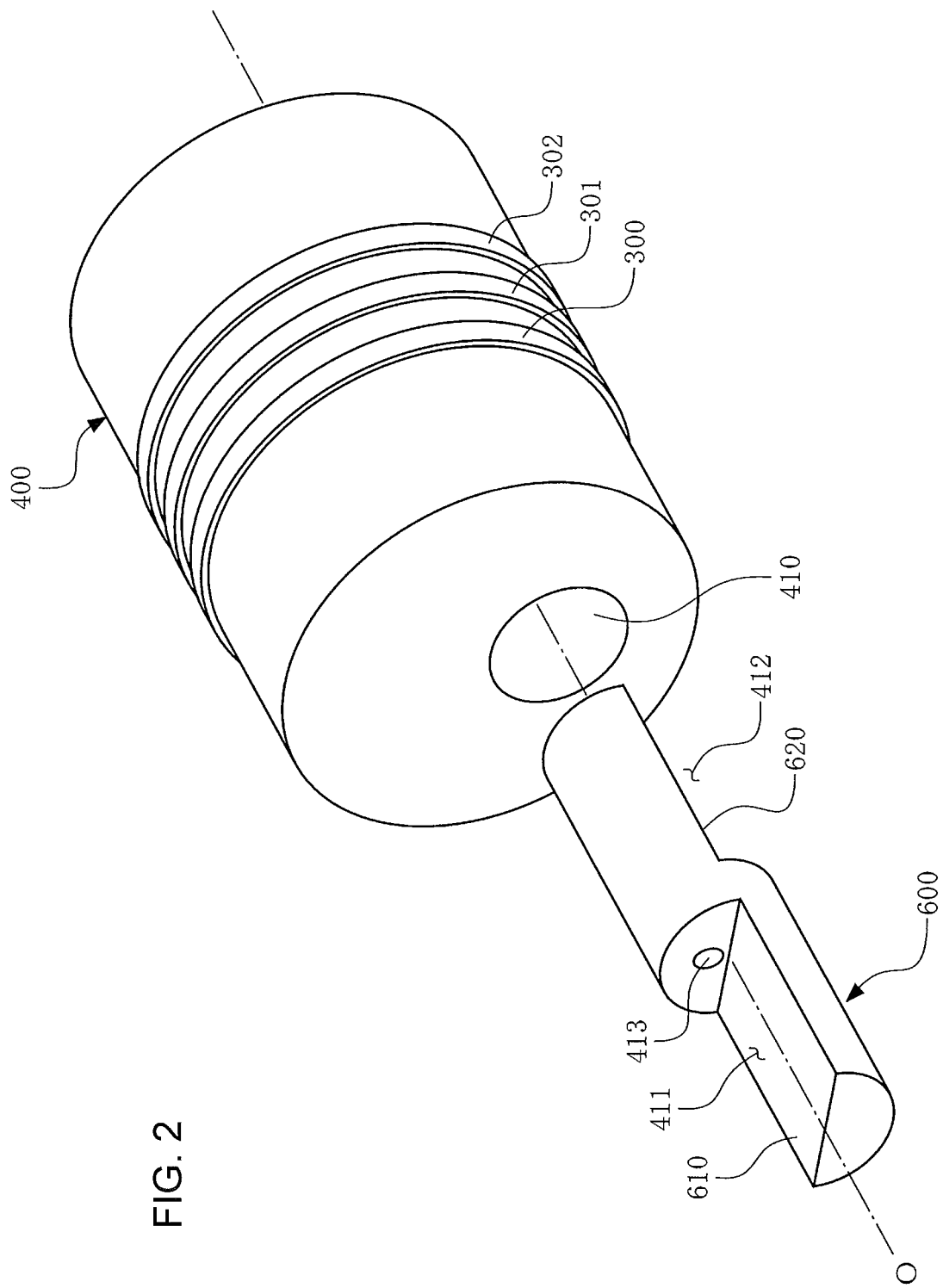
FIG. 2 is a perspective view illustrating a bobbin and a rotor in the first embodiment of the magnetic material concentration measuring device of the present disclosure.

In the example of FIG. 1 and FIG. 2, the exciting coils 300 and 302 are wound in directions opposite to each other and are connected in series, and alternating voltage is applied to the exciting coils 300 and 302.

The output coil 301 is provided between the two exciting coils 300 and 302 in proximity thereto, and an alternating voltage signal is output as a primary output signal from the output coil 301. However, in order to reduce an influence on the measurement accuracy in the case where the relative position of a rotor 600 and the output coil 301 deviates in an axis line O direction of the rotor 600 due to a temperature change and vibrations, the output coil 301 may be divided in two and provided so as to be shifted in the axis line O direction of the rotor 600.

The exciting coils 300 and 302 and the output coil 301 are connected to a signal processor 500, and the signal processor 500 obtains the concentration of the magnetic material on the basis of a change in the alternating voltage signal (primary output signal) output from the output coil 301.

An eccentric hole 410 that eccentrically extends so as to penetrate in an axis line direction of the bobbin 400 is formed in the bobbin 400.

The rotor 600 is rotatably fitted in the eccentric hole 410 about the eccentric axis line O. The material of the rotor 600 may be a non-magnetic substance (having a relative magnetic permeability of roughly 1).

A first cutout part 610 and a second cutout part 620 are formed in the rotor 600.

The first cutout part 610 forms a first flow passage 411 semicircular in cross-section, on one end side in the eccentric axis line O direction of the rotor 600.

The second cutout part 620 forms a second flow passage 412 semicircular in cross-section, on another end side in the eccentric axis line O direction of the rotor 600, and the second flow passage 412 is shifted by 180 degrees in a rotor 600 rotation direction with respect to the first cutout part 610.

Further, a communication passage 413 is formed in the rotor 600 so as to connect the first flow passage 411 and the second flow passage 412.

Figure 3A:
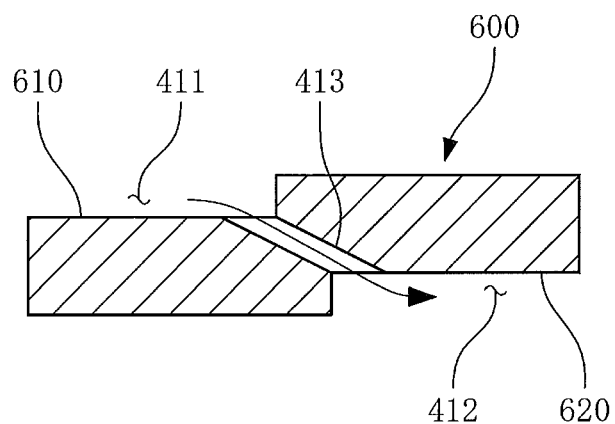
FIG. 3A is a cross-sectional view illustrating a modification of the rotor in the first embodiment of the magnetic material concentration measuring device of the present disclosure.
Figure 3B:
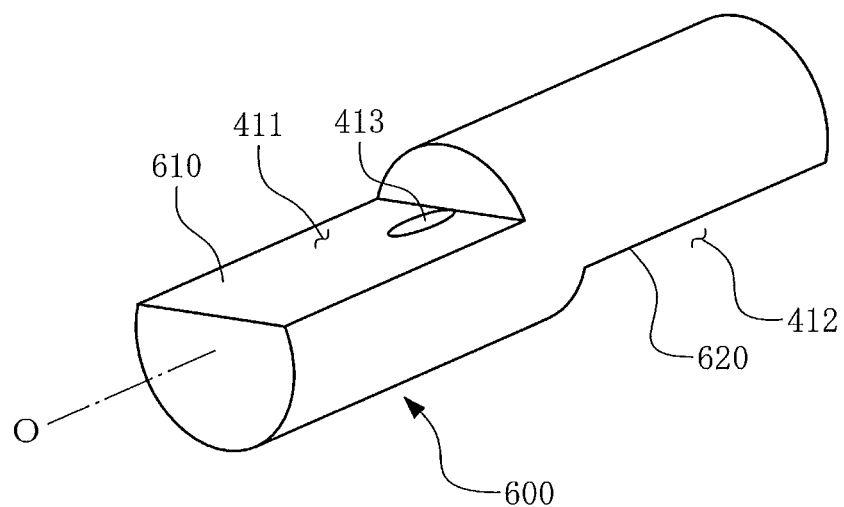
FIG. 3B is a perspective view illustrating the modification of the rotor in the first embodiment of the magnetic material concentration measuring device of the present disclosure.

Note that the first flow passage 411 and the second flow passage 412 are not necessarily limited to the semicircular shape in cross-section. As illustrated in FIG. 3A and FIG. 3B, the thickness of the rotor 600 can be made larger, and the first flow passage 411 and the second flow passage 412 each can have a cross-sectional shape that is surrounded by: a chord shorter than the diameter; and a circular arc connecting both the ends of the chord, the cross-sectional shape having an area smaller than the semicircle.

The rotor 600 is rotationally driven by a transfer drive mechanism 700 that circulates the fluid through the first flow passage 411, the communication passage 413, and the second flow passage 412.

The transfer drive mechanism 700 includes a drive device 710, a drive shaft 720, and a spiral blade 730.

The drive shaft 720 is rotationally driven by the drive device 710 such as a motor, and is connected to the one end side and the another end side of the rotor 600 so as to extend in the eccentric axis line O direction.

The spiral blade 730 is provided on an outer circumference of the drive shaft 720.

Figure 4:
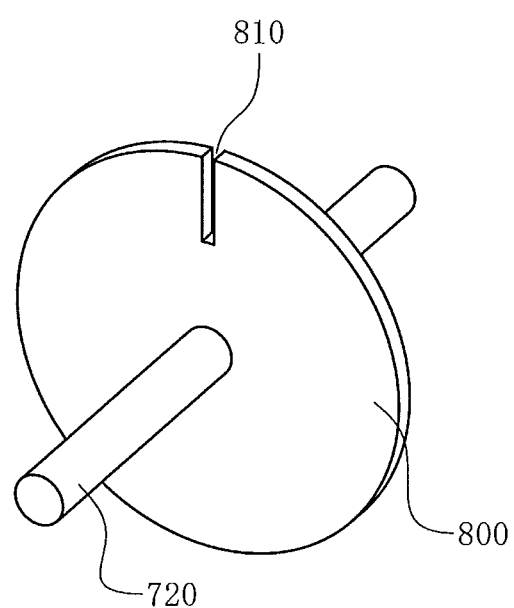
FIG. 4 is a perspective view illustrating a disk of a rotation angle detector in the first embodiment of the magnetic material concentration measuring device of the present disclosure.

As illustrated in FIG. 1 and FIG. 4, a disk 800 is provided to the drive shaft 720, and a slit 810 that extends in the radial direction is formed at a given position in the circumferential direction in a peripheral portion of the disk 800. When the drive shaft 720 is rotated, the slit 810 of the disk 800 is detected by a rotation angle detector 820, whereby the rotation angle of the rotor 600 is grasped by the signal processor 500.

Note that the rotor 600 and the spiral blade 730 are provided inside of a cylindrical member 900. The material of the cylindrical member 900 may be a non-magnetic substance (having a relative magnetic permeability of roughly 1). However, the cylindrical member 900 can be omitted.

Next, operations of the first embodiment are described.

When the drive shaft 720 is rotationally driven by the drive device 710 of the transfer drive mechanism 700, the rotor 600 is rotated about the eccentric axis line O, and the fluid containing the magnetic material is guided by the spiral blade 730 from the inflow pipe 110 forming the flow passage 100 to the inside of the inflow casing 210. However, in the case where the bobbin 400 and the rotor 600 are provided in the middle of the flow passage 100 through which the fluid containing the magnetic material is circulated by raising the pressure of the fluid by a pump or the like (not illustrated), it goes without saying that the transfer drive mechanism 700 does not necessarily need to be provided.

When the drive shaft 720 is rotated, the slit 810 of the disk 800 is detected by the rotation angle detector 820, and the rotation angle of the rotor 600 is grasped by the signal processor 500.

The fluid containing the magnetic material that has been guided to the inside of the inflow casing 210 circulates through the first flow passage 411, the communication passage 413, and the second flow passage 412, then passes through the outflow casing 220 and the nozzle part 221, and is guided to the outflow pipe 120.

Figure 5:
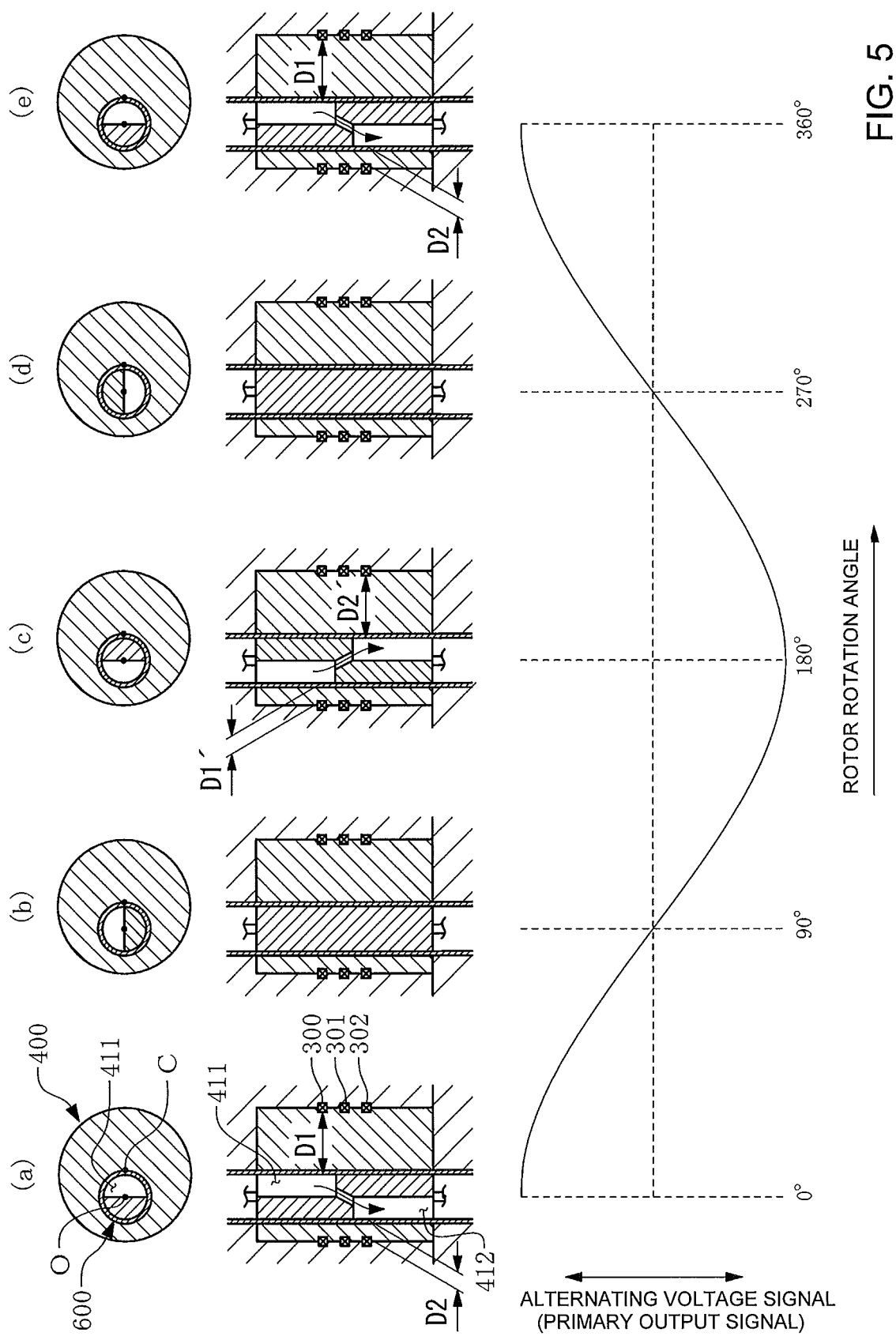
FIG. 5 is a chart illustrating a relation between a rotation angle of the rotor and strength of an alternating voltage signal in the first embodiment of the magnetic material concentration measuring device of the present disclosure.

Here, FIG. 5 illustrates states of the first flow passage 411 and the second flow passage 412 that change in accordance with the rotation of the rotor 600, along a transverse cross-section and a longitudinal cross-section including the eccentric axis line O and a central axis C of the bobbin 400.

In the case where the state illustrated in (a) in FIG. 5 is set as a position at which the rotation angle of the rotor 600 is 0 degrees, the distance via only the bobbin 400 between the fluid (first flow passage 411) and the exciting coil 300 is D1, and the distance between the fluid (second flow passage 412) and the exciting coil 302 is D2, along the longitudinal cross-section including the eccentric axis line O and the central axis C of the bobbin 400.

Further, in the case where the state illustrated in (b) in FIG. 5 is set as a position at which the rotation angle of the rotor 600 is 90 degrees, the first flow passage 411 and the second flow passage 412 of the fluid do not exist along the longitudinal cross-section including the eccentric axis line O and the central axis C of the bobbin 400.

Further, in the case where the state illustrated in (c) in FIG. 5 is set as a position at which the rotation angle of the rotor 600 is 180 degrees, the distance via only the bobbin 400 between the fluid (first flow passage 411) and the exciting coil 300 is D1' (<D1), and the distance between the fluid (second flow passage 412) and the exciting coil 302 is D2' (>D2), along the longitudinal cross-section including the eccentric axis line O and the central axis C of the bobbin 400.

Further, in the case where the state illustrated in (d) in FIG. 5 is set as a position at which the rotation angle of the rotor 600 is 270 degrees, similarly to the position of 90 degrees, the first flow passage 411 and the second flow passage 412 of the fluid do not exist along the longitudinal cross-section including the eccentric axis line O and the central axis C of the bobbin 400.

Still further, in the case where the state illustrated in (e) in FIG. 5 is set as a position at which the rotation angle of the rotor 600 is 360 degrees, similarly to the position of 0 degrees, the distance via only the bobbin 400 between the fluid (first flow passage 411) and the exciting coil 300 is D1, and the distance between the fluid (second flow passage 412) and the exciting coil 302 is D2, along the longitudinal cross-section including the eccentric axis line O and the central axis C of the bobbin 400.

Generally, a magnetic field strength H [A/m] at a point that is away by r [m] from a straight conducting wire when a current of I [A] is fed to the straight conducting wire is as follows.

$$H = I/2\pi r$$

That is, the magnetic field strength H is inversely proportional to: the distance between the fluid (first flow passage 411) and the exciting coil 300; and the distance between the fluid (second flow passage 412) and the exciting coil 302.

With the application of such a relation as described above, if the distance between the fluid (first flow passage 411) and the exciting coil 300 and the distance between the fluid (second flow passage 412) and the exciting coil 302 are changed by rotating the rotor 600, the strength and phase of the alternating voltage signal (primary output signal) of the output coil 301 change depending on the rotation angle of the rotor 600.

Then, the change in the strength and phase of the alternating voltage signal (primary output signal) correlates with the concentration of the magnetic material contained in the fluid.

That is, the signal processor 500 can obtain the concentration of the magnetic material on the basis of the change in the alternating voltage signal (primary output signal) output from the output coil 301, if the signal processor 500 measures, for example, the following results: as illustrated in (a) in FIG. 5 (or (e) in FIG. 5), the magnitude of the change in the alternating voltage signal (primary output signal) is at its maximum on the positive side at the position at which the rotation angle of the rotor 600 is 0 degrees (or 360 degrees); as illustrated in (b) in FIG. 5 (or (d) in FIG. 5), the magnitude of the change in the alternating voltage signal (primary output signal) is neither positive nor negative, in other words, zero at the position at which the rotation angle of the rotor 600 is 90 degrees (or 270 degrees); and, as illustrated in (c) in FIG. 5, the magnitude of the change in the alternating voltage signal (primary output signal) is at its maximum on the negative side at the position at which the rotation angle of the rotor 600 is 180 degrees.

However, the rotation angle of the rotor 600 does not necessarily need to be grasped by the signal processor 500, and, even if the disk 800 and the rotation angle detector 820 are omitted, the concentration of the magnetic material can be detected on the basis of the amplitude of the alternating voltage signal (primary output signal). Further, the second cutout part 620 does not necessarily need to be formed so as to be shifted by 180 degrees in the rotor 600 rotation direction with respect to the first cutout part 610, and the second cutout part 620 can be formed so as to be shifted by an angle other than 180 degrees. This is confirmed by an experiment conducted by the present inventors.

In the case of the first embodiment, unlike the conventional case, the need to use the mechanism that converts the rotating motion into the reciprocating motion of the piston is eliminated, and there are fewer restrictions in the installation of the magnetic material concentration measuring device.

Further, unlike the conventional case where the fluid is guided into/out of the flow passage by the reciprocating motion of the piston, the fluid circulates in one direction while being easily replaced, and the accuracy of a measurement value can thus be improved.

In this way, the degree of freedom in the installation can be increased, and the enhancement in the accuracy of a measurement value can be achieved.

Figure 6:
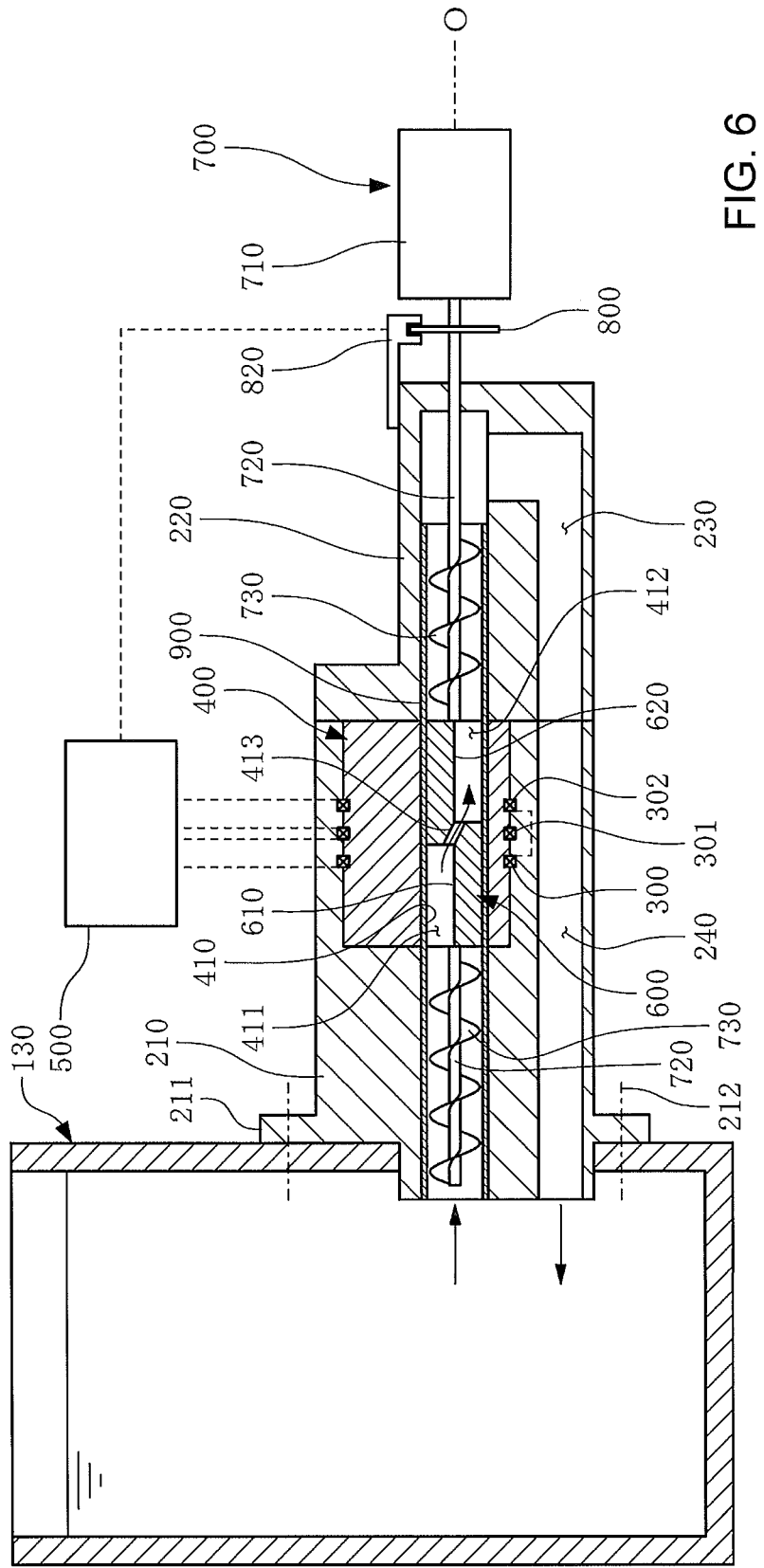
FIG. 6 is a cross-sectional view illustrating a modification of the first embodiment of the magnetic material concentration measuring device of the present disclosure.

FIG. 6 illustrates a modification of the first embodiment of the magnetic material concentration measuring device of the present disclosure, and, in this drawing, elements denoted by the same reference signs as those in FIG. 1 to FIG. 5 represent the same elements.

In the case of the modification illustrated in FIG. 6, the magnetic material concentration measuring device is attached to a container 130 in which the fluid is stored. The flange 211 of the inflow casing 210 is connected to a side surface of the container 130 by the fastening member 212. Circulation flow passages 230 and 240 that return, to the container 130, the fluid that has been guided thereinto from the container 130 are respectively formed in the outflow casing 220 and the inflow casing 210.

Note that the magnetic material concentration measuring device may be attached to not the side surface of the container 130 but a bottom surface of the container 130. Further, a nozzle (not illustrated) may be provided so as to protrude from the side surface or the bottom surface of the container 130, and the flange 211 may be connected to the nozzle.

Next, operations of the modification illustrated in FIG. 6 are described.

When the drive shaft 720 is rotationally driven by the drive device 710 of the transfer drive mechanism 700, the rotor 600 is rotated about the eccentric axis line O, and the fluid containing the magnetic material is guided by the spiral blade 730 from the container 130 to the inside of the inflow casing 210.

When the drive shaft 720 is rotated, similarly to the first embodiment, the slit 810 of the disk 800 is detected by the rotation angle detector 820, and the rotation angle of the rotor 600 is grasped by the signal processor 500. However, it goes without saying that the rotation angle of the rotor 600 does not necessarily need to be grasped by the signal processor 500.

The fluid containing the magnetic material that has been guided to the inside of the inflow casing 210 circulates through the first flow passage 411, the communication passage 413, and the second flow passage 412, then passes through the outflow casing 220 and the circulation flow passages 230 and 240, and is returned to the container 130.

Here, the states of the first flow passage 411 and the second flow passage 412 along with the rotation of the rotor 600 change as illustrated in (a) in FIG. 5 to (e) in FIG. 5, and the signal processor 500 can obtain the concentration of the magnetic material on the basis of the change in the alternating voltage signal output from the output coil 301, with the application of the fact that the magnetic field strength H is inversely proportional to: the distance between the fluid (first flow passage 411) and the exciting coil 300; and the distance between the fluid (second flow passage 412) and the exciting coil 302.

Similarly to the first embodiment, also in the case of the modification illustrated in FIG. 6, unlike the conventional case, the need to use the mechanism that converts the rotating motion into the reciprocating motion of the piston is eliminated, and there are fewer restrictions in the installation of the magnetic material concentration measuring device.

Further, unlike the conventional case where the fluid is guided into/out of the flow passage by the reciprocating motion of the piston, the fluid that has been drawn from the container 130 circulates in one direction to be returned to the container 130 while being smoothly replaced, and the accuracy of a measurement value can thus be improved.

In this way, also in the modification illustrated in FIG. 6, the degree of freedom in the installation can be increased, and the enhancement in the accuracy of a measurement value can be achieved.

Figure 7:
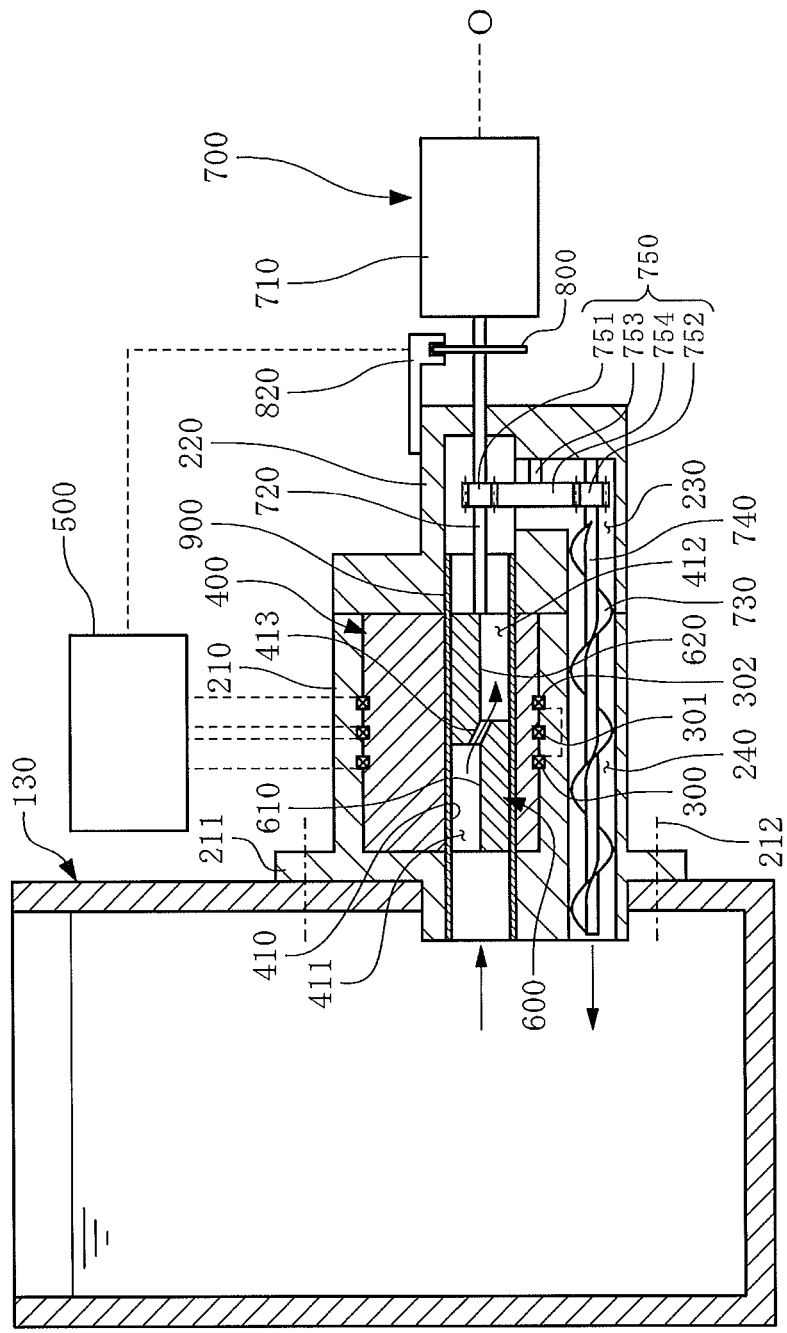
FIG. 7 is a cross-sectional view illustrating a second embodiment of the magnetic material concentration measuring device of the present disclosure.

FIG. 7 illustrates a second embodiment of the magnetic material concentration measuring device of the present disclosure, and, in this drawing, elements denoted by the same reference signs as those in FIG. 6 represent the same elements.

In the second embodiment illustrated in FIG. 7, the transfer drive mechanism 700 is configured by the drive device 710, the drive shaft 720, a transfer shaft 740, a transmission mechanism 750, and the spiral blade 730.

The drive shaft 720 is rotationally driven by the drive device 710 and is connected to the rotor 600 so as to extend in the eccentric axis line O direction.

The transfer shaft 740 is provided inside of the circulation flow passages 230 and 240 in parallel with the drive shaft 720. Note that the transfer shaft 740 is supported by a bearing (not illustrated) rotatably about an axis line thereof.

The transmission mechanism 750 includes: a driving gear 751 fitted to the drive shaft 720; a driven gear 752 fitted to the transfer shaft 740; an intermediate shaft 753 rotatably provided between the drive shaft 720 and the transfer shaft 740; and an intermediate gear 754 that is fitted to the intermediate shaft 753 and meshes with the driving gear 751 and the driven gear 752, and the transmission mechanism 750 transmits the rotation of the drive shaft 720 to the transfer shaft 740.

In the second embodiment, the spiral blade 730 is provided on an outer circumference of not the drive shaft 720 but the transfer shaft 740.

Next, operations of the second embodiment are described.

When the drive shaft 720 is rotationally driven by the drive device 710 of the transfer drive mechanism 700, the rotor 600 is rotated about the eccentric axis line O, and the transfer shaft 740 provided inside of the circulation flow passages 230 and 240 is rotationally driven via the driving gear 751, the intermediate gear 754, and the driven gear 752 of the transmission mechanism 750.

When the transfer shaft 740 is rotationally driven, the fluid containing the magnetic material is guided by the spiral blade 730 from the container 130 to the inside of the inflow casing 210.

When the drive shaft 720 is rotated, similarly to the first embodiment and the modification thereof, the slit 810 of the disk 800 is detected by the rotation angle detector 820, and the rotation angle of the rotor 600 is grasped by the signal processor 500. However, it goes without saying that the rotation angle of the rotor 600 does not necessarily need to be grasped by the signal processor 500.

The fluid containing the magnetic material that has been guided to the inside of the inflow casing 210 circulates through the first flow passage 411, the communication passage 413, and the second flow passage 412, then passes through the outflow casing 220 and the circulation flow passages 230 and 240, and is returned to the container 130.

Here, the states of the first flow passage 411 and the second flow passage 412 along with the rotation of the rotor 600 change as illustrated in (a) in FIG. 5 to (e) in FIG. 5, and the signal processor 500 can obtain the concentration of the magnetic material on the basis of the change in the alternating voltage signal output from the output coil 301, with the application of the fact that the magnetic field strength H is inversely proportional to: the distance between the fluid (first flow passage 411) and the exciting coil 300; and the distance between the fluid (second flow passage 412) and the exciting coil 302.

Similarly to the first embodiment and the modification thereof, also in the case of the second embodiment illustrated in FIG. 7, unlike the conventional case, the need to use the mechanism that converts the rotating motion into the reciprocating motion of the piston is eliminated, and there are fewer restrictions in the installation of the magnetic material concentration measuring device.

Further, unlike the conventional case where the fluid is guided into/out of the flow passage by the reciprocating motion of the piston, the fluid that has been drawn from the container 130 circulates in one direction to be returned to the container 130 while being smoothly replaced, and the accuracy of a measurement value can thus be improved.

In this way, also in the second embodiment illustrated in FIG. 7, the degree of freedom in the installation can be increased, and the enhancement in the accuracy of a measurement value can be achieved.

Figure 8:
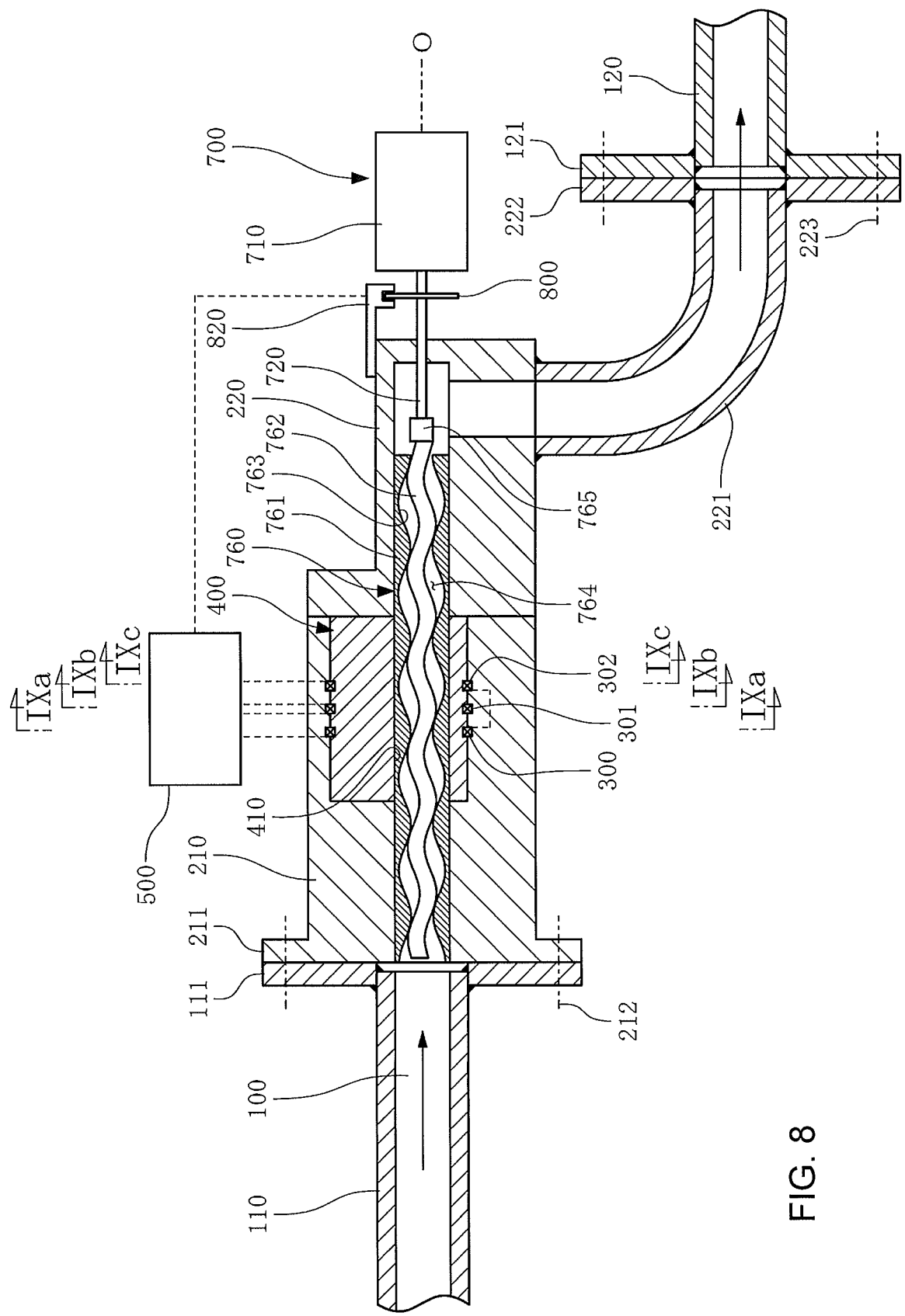
FIG. 8 is a cross-sectional view illustrating a third embodiment of the magnetic material concentration measuring device of the present disclosure.
Figure 9A:
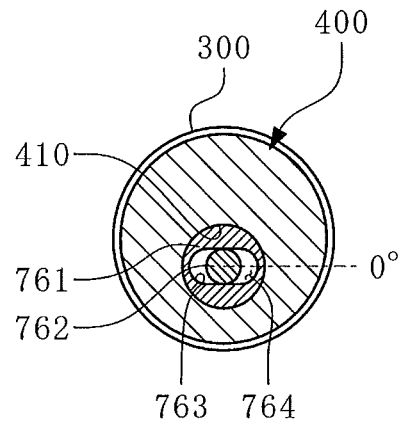
FIG. 9A is a cross-sectional view illustrating a cavity of a uniaxial eccentric screw pump in the third embodiment of the magnetic material concentration measuring device of the present disclosure, and is a cross-sectional view taken along IXa-IXa in FIG. 8.
Figure 9B:
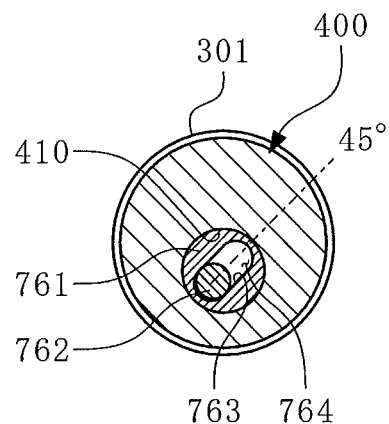
FIG. 9B is a cross-sectional view illustrating the cavity of the uniaxial eccentric screw pump in the third embodiment of the magnetic material concentration measuring device of the present disclosure, and is a cross-sectional view taken along IXb-IXb in FIG. 8.
Figure 9C:
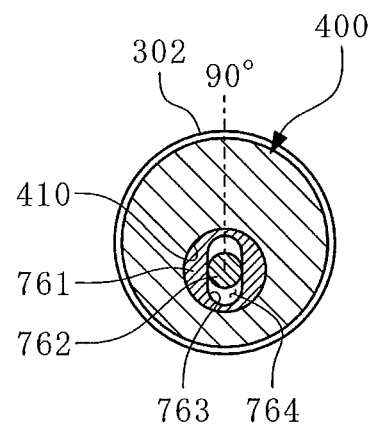
FIG. 9C is a cross-sectional view illustrating the cavity of the uniaxial eccentric screw pump in the third embodiment of the magnetic material concentration measuring device of the present disclosure, and is a cross-sectional view taken along IXc-IXc in FIG. 8.

FIG. 8 to FIG. 9C illustrate a third embodiment of the magnetic material concentration measuring device of the present disclosure, and, in these drawings, elements denoted by the same reference signs as those in FIG. 1 represent the same elements.

In the third embodiment illustrated in FIG. 8 to FIG. 9C, a uniaxial eccentric screw pump 760 is used as the transfer drive mechanism 700.

The uniaxial eccentric screw pump 760 is fitted in the eccentric hole 410 of the bobbin 400, circulates the fluid, and includes a stator 761 and a rotor 762.

A spiral flow passage 763 is formed inside of the stator 761.

The rotor 762 is rotatably fitted in the stator 761 and forms a continuous cavity 764 independent of the spiral flow passage 763.

As illustrated in FIG. 9A and FIG. 9C, the exciting coils 300 and 302 between which the output coil 301 is located are respectively wound at outer circumferential positions of the bobbin 400 corresponding to positions with respect to each of which the cavity 764 is formed so as to be shifted by 90 degrees in the rotation direction of the rotor 762. The output coil 301 is wound midway between the exciting coils 300 and 302, that is, as illustrated in FIG. 9B, at an outer circumferential position of the bobbin 400 corresponding to a position at which the cavity 764 is formed so as to be shifted by 45 degrees in the rotation direction of the rotor 762.

Note that the rotor 762 is coupled via a universal joint 765 to the drive shaft 720 rotationally driven by the drive device 710 such a motor.

Next, operations of the third embodiment are described.

When the drive shaft 720 is rotationally driven by the drive device 710 of the transfer drive mechanism 700, the rotor 762 is rotated via the universal joint about the eccentric axis line O, and the fluid containing the magnetic material is guided by the rotor 762 from the inflow pipe 110 forming the flow passage 100 into the spiral flow passage 763 of the stator 761 located inside of the inflow casing 210.

The fluid containing the magnetic material that has been guided into the spiral flow passage 763 of the stator 761 located inside of the inflow casing 210 circulates through the continuous cavity 764 independently formed in the spiral flow passage 763 along with the rotation of the rotor 762, then passes through the outflow casing 220 and the nozzle part 221, and is guided to the outflow pipe 120.

When the drive shaft 720 is rotated, similarly to the first embodiment, the modification thereof, and the second embodiment, the slit 810 of the disk 800 is detected by the rotation angle detector 820, and the rotation angle of the rotor 600 is grasped by the signal processor 500. However, it goes without saying that the rotation angle of the rotor 600 does not necessarily need to be grasped by the signal processor 500.

Here, the cross-section of the stator 761 at the position at which the exciting coil 300 is wound is illustrated in FIG. 9A, the cross-section of the stator 761 at the position at which the output coil 301 is wound is illustrated in FIG. 9B, and the cross-section of the stator 761 at the position at which the exciting coil 302 is wound is illustrated in FIG. 9C. That is, when the fluid containing the magnetic material circulates through the continuous cavity 764 along with the rotation of the rotor 762, there is a change in the distance between the fluid and the exciting coil 300 and the distance between the fluid and the exciting coil 302. Hence, the alternating voltage signal output from the output coil 301 changes, and the concentration of the magnetic material can be obtained on the basis of the change in the alternating voltage signal output from the output coil 301.

Similarly to the first embodiment, the modification thereof, and the second embodiment, also in the case of the third embodiment illustrated in FIG. 8 to FIG. 9C, unlike the conventional case, the need to use the mechanism that converts the rotating motion into the reciprocating motion of the piston is eliminated, and there are fewer restrictions in the installation of the magnetic material concentration measuring device.

Further, unlike the conventional case where the fluid is guided into/out of the flow passage by the reciprocating motion of the piston, the fluid that has been drawn from the container 130 circulates in one direction to be returned to the container 130 while being smoothly replaced, and the accuracy of a measurement value can thus be improved.

In this way, also in the third embodiment illustrated in FIG. 8 to FIG. 9C, the degree of freedom in the installation can be increased, and the enhancement in the accuracy of a measurement value can be achieved.

Note that, in the third embodiment illustrated in FIG. 8 to FIG. 9C, similarly to the first embodiment illustrated in FIG. 1, the magnetic material concentration measuring device can be attached to the container 130 in which the fluid is stored, as in the modification illustrated in FIG. 6.

Figure 10:
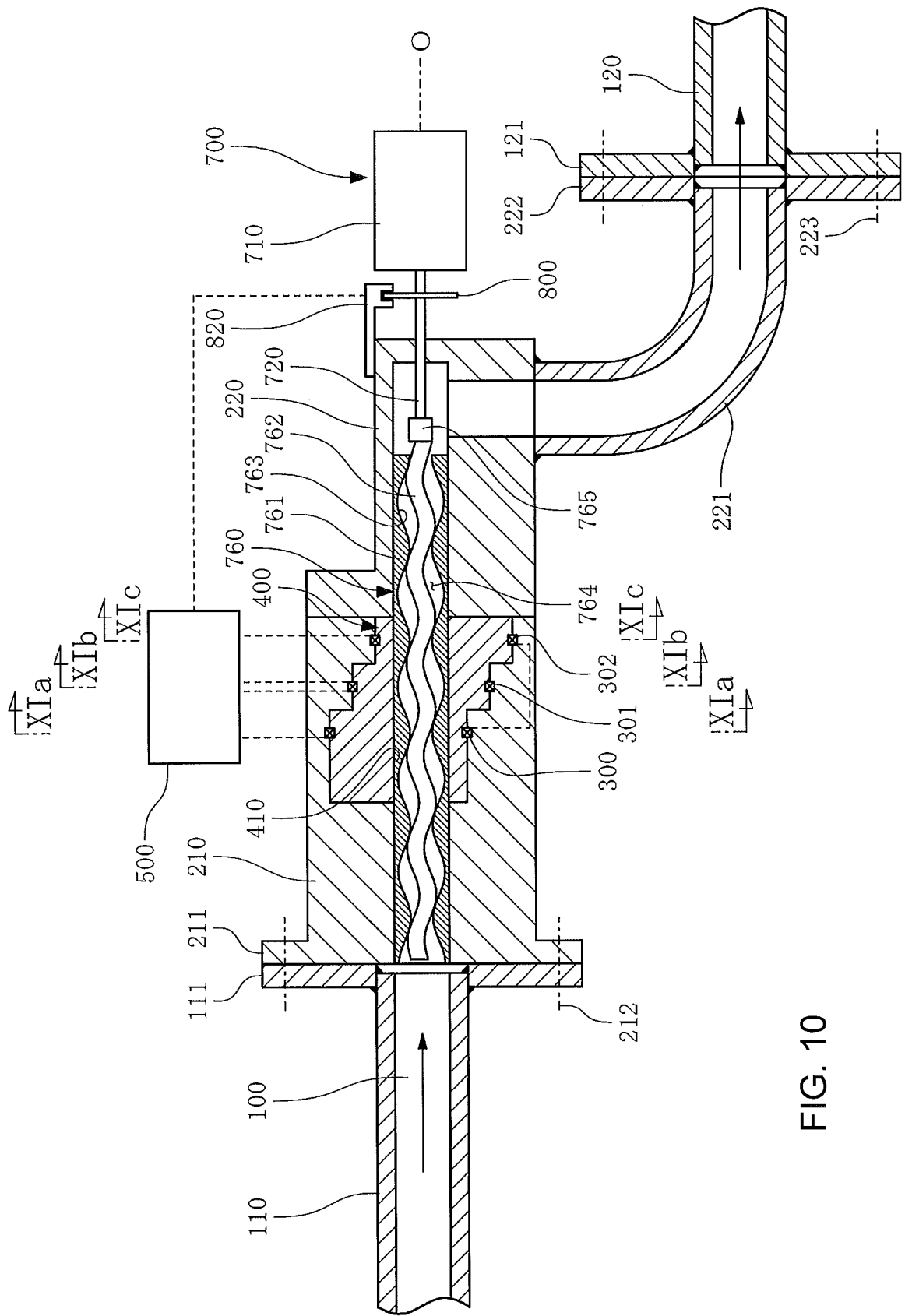
FIG. 10 is a cross-sectional view illustrating a modification of the third embodiment of the magnetic material concentration measuring device of the present disclosure.
Figure 11A:
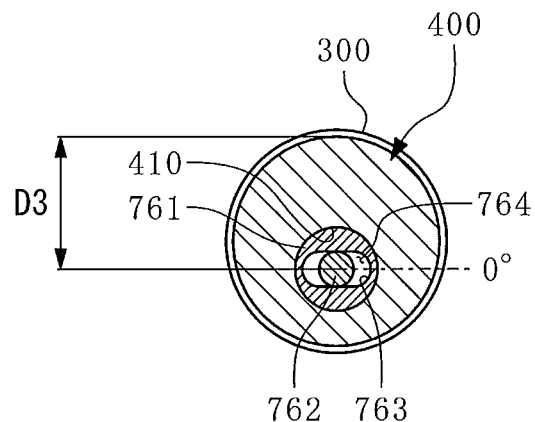
FIG. 11A is a cross-sectional view illustrating a cavity of a uniaxial eccentric screw pump in the modification of the third embodiment of the magnetic material concentration measuring device of the present disclosure, and is a cross-sectional view taken along XIa-XIa in FIG. 10.
Figure 11B:
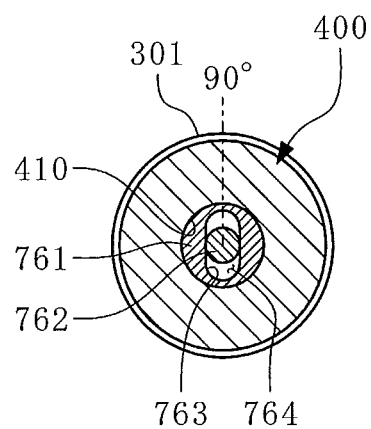
FIG. 11B is a cross-sectional view illustrating the cavity of the uniaxial eccentric screw pump in the modification of the third embodiment of the magnetic material concentration measuring device of the present disclosure, and is a cross-sectional view taken along XIb-XIb in FIG. 10.
Figure 11C:
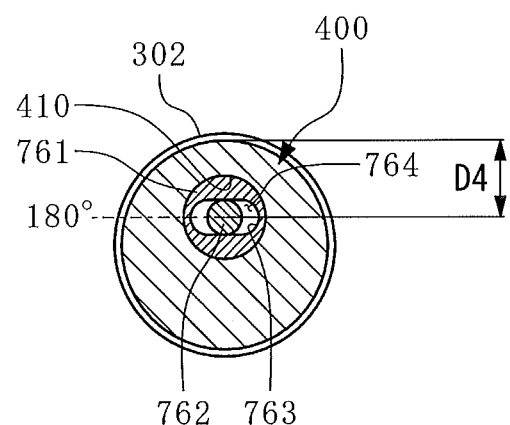
FIG. 11C is a cross-sectional view illustrating the cavity of the uniaxial eccentric screw pump in the modification of the third embodiment of the magnetic material concentration measuring device of the present disclosure, and is a cross-sectional view taken along XIc-XIc in FIG. 10.
Figure 12:
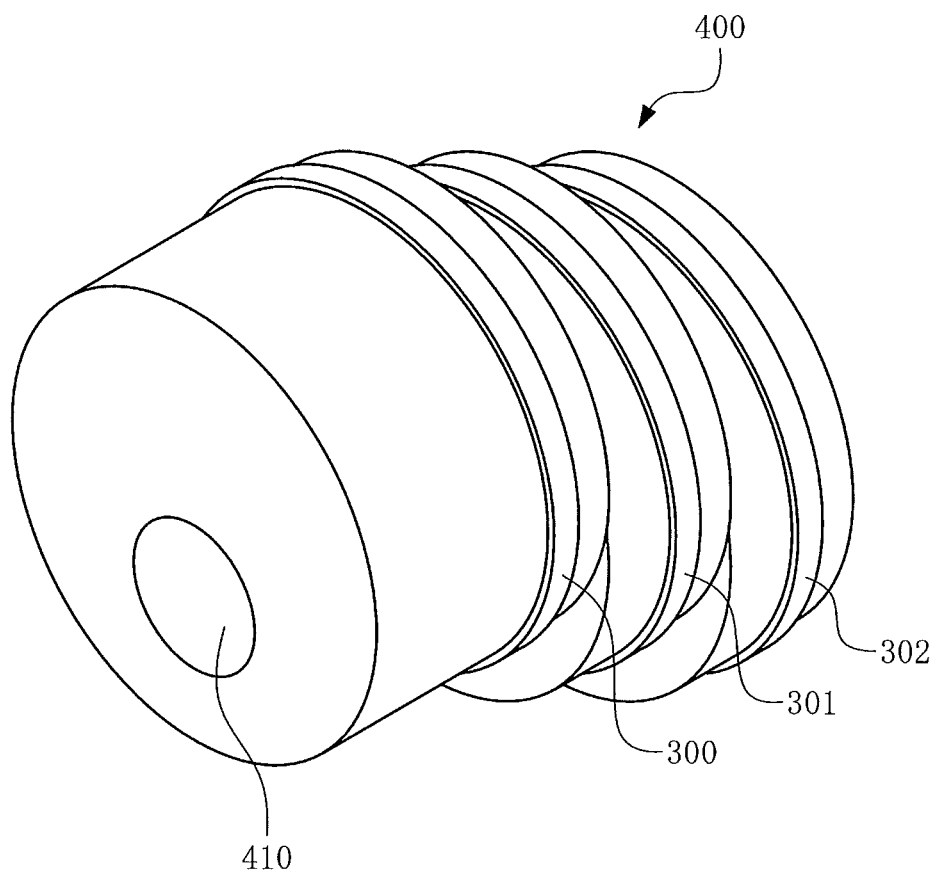
FIG. 12 is a perspective view illustrating a bobbin in the modification of the third embodiment of the magnetic material concentration measuring device of the present disclosure.

FIG. 10 to FIG. 12 illustrate a modification of the third embodiment of the magnetic material concentration measuring device of the present disclosure, and, in these drawings, elements denoted by the same reference signs as those in FIG. 8 to FIG. 9C represent the same elements.

In the modification of the third embodiment illustrated in FIG. 10 to FIG. 12, as illustrated in FIG. 11A and FIG. 11C, the exciting coils 300 and 302 between which the output coil 301 is located are respectively wound such that there is at least a difference between distances D3 and D4 with respect to the cavity 764, at outer circumferential positions of the bobbin 400 corresponding to positions with respect to each of which the cavity 764 is formed so as to be shifted by 180 degrees in the rotation direction of the rotor 762.

The output coil 301 is wound midway between the exciting coils 300 and 302, that is, as illustrated in FIG. 11B, at an outer circumferential position of the bobbin 400 corresponding to a position at which the cavity 764 is formed so as to be shifted by 90 degrees in the rotation direction of the rotor 762.

Note that, in order to make the difference between the distances D3 and D4 of the exciting coils 300 and 302 with respect to the cavity 764, as illustrated in FIG. 10 and FIG. 12, the bobbin 400 is configured by a columnar member through which the eccentric hole 410 penetrates, the columnar member having a shape in which portions around which the exciting coil 300, the output coil 301, and the exciting coil 302 are respectively wound are made eccentric in stages without shifting the position of the eccentric hole 410.

Next, operations of the modification of the third embodiment are described.

When the drive shaft 720 is rotationally driven by the drive device 710 of the transfer drive mechanism 700, the rotor 762 is rotated via the universal joint about the eccentric axis line O, and the fluid containing the magnetic material is guided by the rotor 762 from the inflow pipe 110 forming the flow passage 100 into the spiral flow passage 763 of the stator 761 located inside of the inflow casing 210.

The fluid containing the magnetic material that has been guided into the spiral flow passage 763 of the stator 761 located inside of the inflow casing 210 circulates through the continuous cavity 764 independently formed in the spiral flow passage 763 along with the rotation of the rotor 762, then passes through the outflow casing 220 and the nozzle part 221, and is guided to the outflow pipe 120.

When the drive shaft 720 is rotated, the slit 810 of the disk 800 is detected by the rotation angle detector 820, and the rotation angle of the rotor 600 is grasped by the signal processor 500. However, it goes without saying that the rotation angle of the rotor 600 does not necessarily need to be grasped by the signal processor 500.

The above-mentioned behavior is similar to that of the third embodiment.

However, in the case of the modification of the third embodiment, the cross-section of the stator 761 at the position at which the exciting coil 300 is wound is as illustrated in FIG. 11A, the cross-section of the stator 761 at the position at which the output coil 301 is wound is as illustrated in FIG. 11B, and the cross-section of the stator 761 at the position at which the exciting coil 302 is wound is as illustrated in FIG. 11C.

Here, although the cross-sectional shape of the cavity 764 illustrated in FIG. 11A and the cross-sectional shape of the cavity 764 illustrated in FIG. 11C are the same as each other, as illustrated in FIG. 10 and FIG. 12, the portions of the bobbin 400 around which the exciting coil 300, the output coil 301, and the exciting coil 302 are respectively wound are made eccentric in stages.

Therefore, when the fluid containing the magnetic material circulates through the continuous cavity 764 along with the rotation of the rotor 762, there is a change in the distance between the fluid and the exciting coil 300, which is D3, and the distance between the fluid and the exciting coil 302, which is D4. Hence, the alternating voltage signal output from the output coil 301 changes, and the concentration of the magnetic material can be obtained on the basis of the change in the alternating voltage signal output from the output coil 301.

Also in the case of the modification of the third embodiment illustrated in FIG. 10 to FIG. 12, similarly to the third embodiment, unlike the conventional case, the need to use the mechanism that converts the rotating motion into the reciprocating motion of the piston is eliminated, and there are fewer restrictions in the installation of the magnetic material concentration measuring device.

Further, unlike the conventional case where the fluid is guided into/out of the flow passage by the reciprocating motion of the piston, the fluid that has been drawn from the container 130 circulates in one direction to be returned to the container 130 while being smoothly replaced, and the accuracy of a measurement value can thus be improved.

In this way, also in the modification of the third embodiment illustrated in FIG. 10 to FIG. 12, the degree of freedom in the installation can be increased, and the enhancement in the accuracy of a measurement value can be achieved.

Note that, in the modification of the third embodiment illustrated in FIG. 10 to FIG. 12, similarly to the first embodiment illustrated in FIG. 1, the magnetic material concentration measuring device can be attached to the container 130 in which the fluid is stored, as in the modification illustrated in FIG. 6.

Then, all the embodiments include the transfer drive mechanism 700 that circulates the fluid through the first flow passage 411, the communication passage 413, and the second flow passage 412 while rotating the rotor 600. Such a configuration is effective in guiding, to the inside of the bobbin 400, the fluid containing the magnetic material that is not circulated because the pressure of the fluid is not raised by a pump or the like.

In the case of the first embodiment illustrated in FIG. 1 and the modification of the first embodiment illustrated in FIG. 6, the transfer drive mechanism 700 includes: the drive shaft 720 that is rotationally driven by the drive device 710 and is connected to the rotor 600 so as to extend in the eccentric axis line O direction; and the spiral blade 730 provided on the outer circumference of the drive shaft 720. According to such a configuration, the drive shaft 720 alone can rotate the spiral blade 730 while rotating the rotor 600, and the fluid containing the magnetic material can be smoothly circulated.

Further, in the case of the second embodiment illustrated in FIG. 7, the transfer drive mechanism 700 includes: the drive shaft 720 that is rotationally driven by the drive device 710 and is connected to the rotor 600 so as to extend in the eccentric axis line O direction; the transfer shaft 740 provided in parallel with the drive shaft 720; the transmission mechanism 750 that transmits the rotation of the drive shaft 720 to the transfer shaft 740; and the spiral blade 730 provided on the outer circumference of the transfer shaft 740. Such a configuration is effective in shortening the entire length of the magnetic material concentration measuring device and further increasing the degree of freedom in the installation, in the case where the magnetic material concentration measuring device is attached to the container 130 in which the fluid is stored and where the fluid is guided from the container 130 to be returned thereto.

Further, in the case of the third embodiment illustrated in FIG. 8 and the modification of the third embodiment illustrated in FIG. 10, the magnetic material concentration measuring device includes: the exciting coils 300 and 302 to which the alternating voltage is applied, the exciting coils 300 and 302 being provided on the outer circumference of the flow passage through which the fluid containing the magnetic material flows; the output coil 301 from which the alternating voltage signal is output, the output coil 301 being provided in proximity to the exciting coils 300 and 302; and the signal processor 500 that obtains the concentration of the magnetic material on the basis of the change in the alternating voltage signal output from the output coil 301, and the magnetic material concentration measuring device includes: the bobbin 400 having the outer circumference around which the exciting coil 300, the output coil 301, and the exciting coil 302 are wound; the eccentric hole 410 that is eccentrically formed so as to penetrate in the axis line direction of the bobbin 400; and the uniaxial eccentric screw pump 760 that is fitted in the eccentric hole 410 and circulates the fluid. Such a configuration makes it possible to constantly transfer the fluid containing the magnetic material without pulsations, and is effective in further improving the accuracy of a measurement value.

Further, in the case of the third embodiment illustrated in FIG. 8 to FIG. 9C, the uniaxial eccentric screw pump 760 includes: the stator 761 inside of which the spiral flow passage 763 is formed; and the rotor 762 that is rotatably fitted in the stator 761 and forms the continuous cavity 764 independent of the spiral flow passage 763, and the exciting coils 300 and 302 between which the output coil 301 is located are respectively wound at the outer circumferential positions of the bobbin 400 corresponding to the positions with respect to each of which the cavity 764 is formed so as to be shifted by 90 degrees in the rotation direction of the rotor 762. According to such a configuration, when the fluid containing the magnetic material circulates through the continuous cavity 764 along with the rotation of the rotor 762, the distance between the fluid and the exciting coil 300 and the distance between the fluid and the exciting coil 302 can be changed, and the concentration of the magnetic material can be obtained on the basis of the change in the alternating voltage signal output from the output coil 301.

Further, in the case of the modification of the third embodiment illustrated in FIG. 10 to FIG. 12, the uniaxial eccentric screw pump 760 includes: the stator 761 inside of which the spiral flow passage 763 is formed; and the rotor 762 that is rotatably fitted in the stator 761 and forms the continuous cavity 764 independent of the spiral flow passage 763, and the exciting coils 300 and 302 between which the output coil 301 is located are respectively wound such that there is at least a difference between the distances D3 and D4 with respect to the cavity 764, at the outer circumferential positions of the bobbin 400 corresponding to the positions with respect to each of which the cavity 764 is formed so as to be shifted by 180 degrees in the rotation direction of the rotor 762. According to such a configuration, when the fluid containing the magnetic material circulates through the continuous cavity 764 along with the rotation of the rotor 762, the alternating voltage signal output from the output coil 301 can be changed by the difference between the distances D3 and D4 between the fluid and the exciting coils 300 and 302, and the concentration of the magnetic material can be obtained on the basis of the change in the alternating voltage signal output from the output coil 301.

Note that the magnetic material concentration measuring device of the present disclosure is not limited to only the above-mentioned embodiments, and can be variously changed within the range not departing from the scope of the present disclosure as a matter of course.

REFERENCE SIGNS LIST 100 flow passage
110 inflow pipe
111 flange
120 outflow pipe
121 flange
130 container
200 measuring device main body
210 inflow casing
211 flange
212 fastening member
220 outflow casing
221 nozzle part 222 flange
223 fastening member
230 circulation flow passage
240 circulation flow passage
300 exciting coil
301 output coil
302 exciting coil
400 bobbin
410 eccentric hole
411 first flow passage
412 second flow passage
413 communication passage
500 signal processor
600 rotor
610 first cutout part
620 second cutout part
700 transfer drive mechanism
710 drive device
720 drive shaft
730 spiral blade
740 transfer shaft
750 transmission mechanism
751 driving gear
752 driven gear
753 intermediate shaft
754 intermediate gear
760 uniaxial eccentric screw pump
761 stator
762 rotor
763 spiral flow passage
764 cavity
765 universal joint
800 disk
810 slit
820 rotation angle detector
900 cylindrical member
C central axis
O eccentric axis line
D3 distance
D4 distance

The invention claimed is:

1. A magnetic material concentration measuring device comprising: exciting coils to which alternating voltage is applied, the exciting coils being provided on an outer circumference of a flow passage through which a fluid containing a magnetic material flows; an output coil from which an alternating voltage signal is output, the output coil being provided in proximity to the exciting coils; and a signal processor that obtains a concentration of the magnetic material on a basis of a change in the alternating voltage signal output from the output coil, the magnetic material concentration measuring device comprising:
   a bobbin having an outer circumference around which the exciting coil, the output coil, and the exciting coil are wound;
   an eccentric hole that is eccentrically formed so as to penetrate in an axis line direction of the bobbin;
   a rotor that is rotatably fitted in the eccentric hole about an eccentric axis line;
   a first cutout part that forms a first flow passage on one end side in an eccentric axis line direction of the rotor;
   a second cutout part that forms a second flow passage whose angle is shifted in a rotor rotation direction with respect to the first cutout part, on another end side in the eccentric axis line direction of the rotor; and
   a communication passage that is formed in the rotor so as to connect the first flow passage and the second flow passage.

2. The magnetic material concentration measuring device according to claim 1, comprising a transfer drive mechanism that circulates the fluid through the first flow passage, the communication passage, and the second flow passage while rotating the rotor.

3. The magnetic material concentration measuring device according to claim 2, wherein the transfer drive mechanism includes:
   a drive shaft that is rotationally driven by a drive device and is connected to the rotor so as to extend in the eccentric axis line direction; and
   a spiral blade provided on an outer circumference of the drive shaft.

4. The magnetic material concentration measuring device according to claim 2, wherein the transfer drive mechanism includes:
   a drive shaft that is rotationally driven by a drive device and is connected to the rotor so as to extend in the eccentric axis line direction;
   a transfer shaft provided in parallel with the drive shaft;
   a transmission mechanism that transmits rotation of the drive shaft to the transfer shaft; and
   a spiral blade provided on an outer circumference of the transfer shaft.

5. A magnetic material concentration measuring device comprising: exciting coils to which alternating voltage is applied, the exciting coils being provided on an outer circumference of a flow passage through which a fluid containing a magnetic material flows; an output coil from which an alternating voltage signal is output, the output coil being provided in proximity to the exciting coils; and a signal processor that obtains a concentration of the magnetic material on a basis of a change in the alternating voltage signal output from the output coil, the magnetic material concentration measuring device comprising:
   a bobbin having an outer circumference around which the exciting coil, the output coil, and the exciting coil are wound;
   an eccentric hole that is eccentrically formed so as to penetrate in an axis line direction of the bobbin; and
   a uniaxial eccentric screw pump that is fitted in the eccentric hole and circulates the fluid.

6. The magnetic material concentration measuring device according to claim 5, wherein
   the uniaxial eccentric screw pump includes:
      a stator inside of which a spiral flow passage is formed; and
      a rotor that is rotatably fitted in the stator and forms a continuous cavity independent of the spiral flow passage, and
   the exciting coils between which the output coil is located are respectively wound at outer circumferential positions of the bobbin corresponding to positions with respect to each of which the cavity is formed so as to be shifted by 90 degrees in a rotor rotation direction.

7. The magnetic material concentration measuring device according to claim 5, wherein
   the uniaxial eccentric screw pump includes:
      a stator inside of which a spiral flow passage is formed; and
      a rotor that is rotatably fitted in the stator and forms a continuous cavity independent of the spiral flow passage, and the exciting coils between which the output coil is located are respectively wound such that there is at least a difference in a distance with respect to the cavity, at outer circumferential positions of the bobbin corresponding to positions with respect to each of which the cavity is formed so as to be shifted by 180 degrees in a rotor rotation direction.

* * * * *